(12) United States Patent
Mason et al.

(10) Patent No.: US 11,419,975 B2
(45) Date of Patent: Aug. 23, 2022

(54) STRUCTURE FOR PACKAGING CONTAINERS FOR PHARMACEUTICAL USE

(71) Applicant: NUOVA OMPI S.R.L., Padua (IT)

(72) Inventors: Diego Mason, Padua (IT); Gianpaolo Bertolin, Padua (IT)

(73) Assignee: NUOVA OMPI S.R.L., Padua (IT)

( * ) Notice: Subject to any disclaimer, the term of this patent is extended or adjusted under 35 U.S.C. 154(b) by 190 days.

(21) Appl. No.: 16/958,221

(22) PCT Filed: Feb. 19, 2019

(86) PCT No.: PCT/IB2019/051319
§ 371 (c)(1),
(2) Date: Jun. 26, 2020

(87) PCT Pub. No.: WO2019/171192
PCT Pub. Date: Sep. 12, 2019

(65) Prior Publication Data
US 2020/0390967 A1    Dec. 17, 2020

(30) Foreign Application Priority Data
Mar. 8, 2018 (IT) .................. 102018000003376

(51) Int. Cl.
*A61M 5/00* (2006.01)

(52) U.S. Cl.
CPC ............ *A61M 5/008* (2013.01); *A61M 5/002* (2013.01)

(58) Field of Classification Search
CPC ....... A61M 5/001; A61M 5/008; A61M 5/002

USPC ................................ 206/363, 364, 365, 370
See application file for complete search history.

(56) References Cited

U.S. PATENT DOCUMENTS

| 2010/0258578 | A1 | 10/2010 | Motadel | |
| 2013/0001117 | A1* | 1/2013 | Liversidge | B65D 25/34 206/370 |
| 2014/0102927 | A1* | 4/2014 | Liversidge | B65D 25/108 206/364 |

(Continued)

FOREIGN PATENT DOCUMENTS

| DE | 102015108066 A1 | 11/2016 |
| EP | 3106188 A1 | 12/2016 |

(Continued)

OTHER PUBLICATIONS

International Search Report for corresponding application PCT/IB2019/051319 filed Feb. 19, 2019; dated Apr. 11, 2019.

*Primary Examiner* — Jacob K Ackun
(74) *Attorney, Agent, or Firm* — Cantor Colburn LLP (57) ABSTRACT

A structure for packaging containers for pharmaceutical use including a support plane fitted with a plurality of seats for housing containers for pharmaceutical use, the seats having main extension axes (X-X), parallel to each other, the seats being delimited by perimeter walls which project from the support plane towards a top side of the structure, where on the side of a top face of the seats, intended to receive in abutment an undercut element of said containers, a raised perimeter of each seat is provided to delimit and surround at least partially an annular pocket, enlarged with respect to the seat and intended to receive in abutment the undercut element of said containers for pharmaceutical use.

26 Claims, 9 Drawing Sheets

(56) References Cited

U.S. PATENT DOCUMENTS

| | | | | |
|---|---|---|---|---|
| 2015/0041349 A1* | 2/2015 | Liversidge | ................ | B01L 9/54 |
| | | | | 206/364 |
| 2019/0038790 A1* | 2/2019 | McLaughlin | ......... | A61M 5/001 |
| 2020/0114063 A1* | 4/2020 | Vivien | .................. | A61M 5/008 |

FOREIGN PATENT DOCUMENTS

| | | |
|---|---|---|
| WO | 2016111698 A1 | 7/2016 |
| WO | 2017132554 A1 | 8/2017 |

* cited by examiner

STRUCTURE FOR PACKAGING CONTAINERS FOR PHARMACEUTICAL USE

TECHNICAL FIELD

The present invention concerns a structure for packaging containers for pharmaceutical use.

BACKGROUND

As is well known, primary containers for pharmaceutical use such as, for example, vials, bottles, tubular injection vials and syringes must be kept in a controlled environment that is isolated from the outside, as well as kept clean and sterile, until their use or their use in treatment processes, in particular, filling and closure.

Structures are known for packaging containers for pharmaceutical use comprising a tray, called a "tub", made of plastic material and with a closed bottom, which supports therein a support plane or matrix (called a "nest"), typically made of plastic material and having a series of housing holes wherein the primary containers for pharmaceutical use are housed vertically.

Some types of primary containers for pharmaceutical use, such as, for example, syringes, may be held in place by the support of the perimeter collar on the edge of the housing holes, while other containers, lacking protruding parts, require special elements to hold them inside the holes.

Such sealed packaging structures (said tubs and nests), appropriately sealed, are in turn placed in containers of a size and weight suitable for handling during packing and unpacking operations.

Such packaging structures (tub and nest) are therefore repeatedly manipulated also by automated mechanical arms to be transported, repositioned, turned over and stored.

For this purpose, the need is felt to create packaging structures that are as light as possible and that guarantee, at the same time, an adequate mechanical rigidity.

In effect, the support planes (nest) in particular tend to flex downwards under their own weight and also, and above all, under the weight of the dozens of primary containers that they must house and support. Such weight increases further when said primary containers are filled with a medical substance.

Such flexing should be limited as much as possible, since the containers lose their mutual parallelism with respect to a vertical direction, perpendicular to the support plane.

Thus, the containers would tend to collide with each other, and the flexing would make the operation of inserting and extracting the containers from the nest, as well as the operation of filling the same containers at the pharmaceutical company, difficult.

This flexing must be avoided or at any rate controlled with extreme precision, since the packaging structures must be handled in an automated way using mechanical arms that could interfere with some of said containers, if they are misplaced/misorientated within the respective seats of the support plane, in particular in the steps of introducing and extracting the primary containers from the nest.

Excessive flexing of the nests therefore increases the risk of impacts between the grippers and the containers and limits the automation possibilities for gripping and handling the containment structures.

Moreover, the deformation of the nests facilitates mutual contact between containers which could chip as a result of impacts, both on the cantilevered bodies and the respective collars.

Impacts must be prevented as they could generate cracks, even micro-cracks, with the consequent risk of subsequent breakage of the containers.

Such impacts, not only to the tubular bodies of the containers but also to their respective gripping collars, must be avoided.

Obviously, the need to reduce the weight of the nest contrasts with the need for rigidity in the containment structures. In effect, weight reduction is normally achieved by discharging material, reducing thicknesses, and creating notches and lightening holes. These measures inevitably weaken the mechanical rigidity of the structure, which tends to deform excessively.

For these reasons, as of today no solutions are known that are able to simultaneously achieve an adequate reduction in weight without affecting the mechanical rigidity of the containment structure of the containers, while at the same time maintaining the mutual parallelism of the containers in a vertical direction, perpendicular to the support plane.

BRIEF SUMMARY

The need is therefore felt to resolve the drawbacks and limitations cited in reference to the known art.

Therefore, there is a need to provide a structure for the packaging of containers for pharmaceutical use that is both light and strong so as to allow a proper grip and handling of the structure itself in a fast and automated way, without running the risk of accidental contact between the gripping device and the containers, as well as between neighboring containers resulting from their misalignment with respect to a vertical direction.

Such requirement is met by a structure for packaging containers for pharmaceutical use as described herein.

DESCRIPTION OF THE DRAWINGS

Further features and advantages of the present invention will become more apparent from the following description provided of the preferred and non-limiting examples of embodiment thereof, wherein.

The elements or parts of elements in common between the embodiments described hereinafter will be indicated at the same numerical references.

DETAILED DESCRIPTION

With reference to the aforementioned figures, an overall view of a structure for packaging containers for pharmaceutical use is collectively indicated at 4.

It should be noted that, for the purposes of protecting the present invention, the specific type of containers for pharmaceutical use is not relevant, meaning containers of various types, sizes and/or materials such as syringes, vials, tube vials, bottles and the like, or medical devices provided or not with means to contain a drug, such as an autoinjector with or without carpule or the like.

Figure 12:
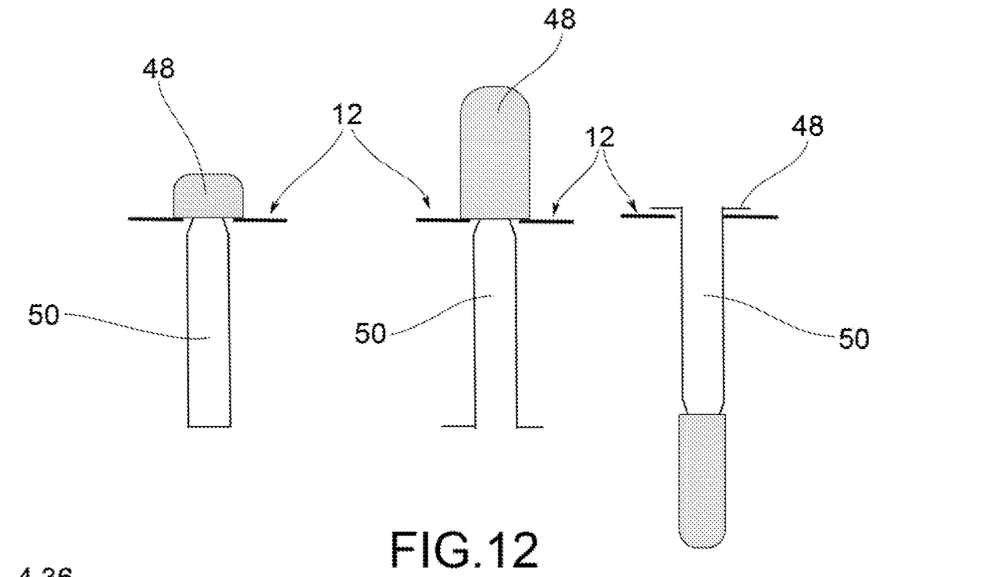
FIG. 12 shows views in cross-section of possible containers for pharmaceutical use supportable by a containment structure according to the present invention.
Figure 13:
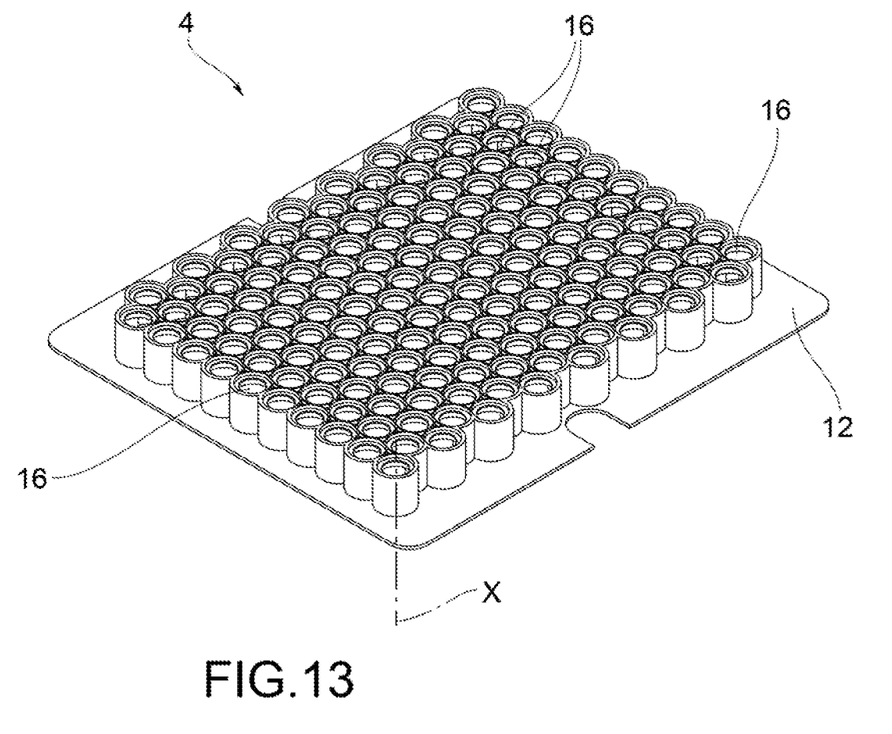
FIG. 13 shows a perspective view from above of a further structure for packaging containers for pharmaceutical use according to the present invention.

For example, some types of containers for pharmaceutical use 20 are shown in FIG. 12.

The structure 4 comprises a tray 8 that accommodates and supports a support plane 12 provided with a plurality of seats 16 for accommodating containers for pharmaceutical use 20.

Typically, the seats 16 have a cylindrical shape with respect to main extension axes X-X, parallel to each other. Said main extension axes are perpendicular to the support plane 12.

The seats 16 are delimited by perimeter walls 24 which project from the support plane 12 towards an upper side 28 of the structure 4.

The top side 28 is in turn opposite to a bottom 32 of the tray 8, wherein said bottom 32 is preferably closed.

Figure 15:
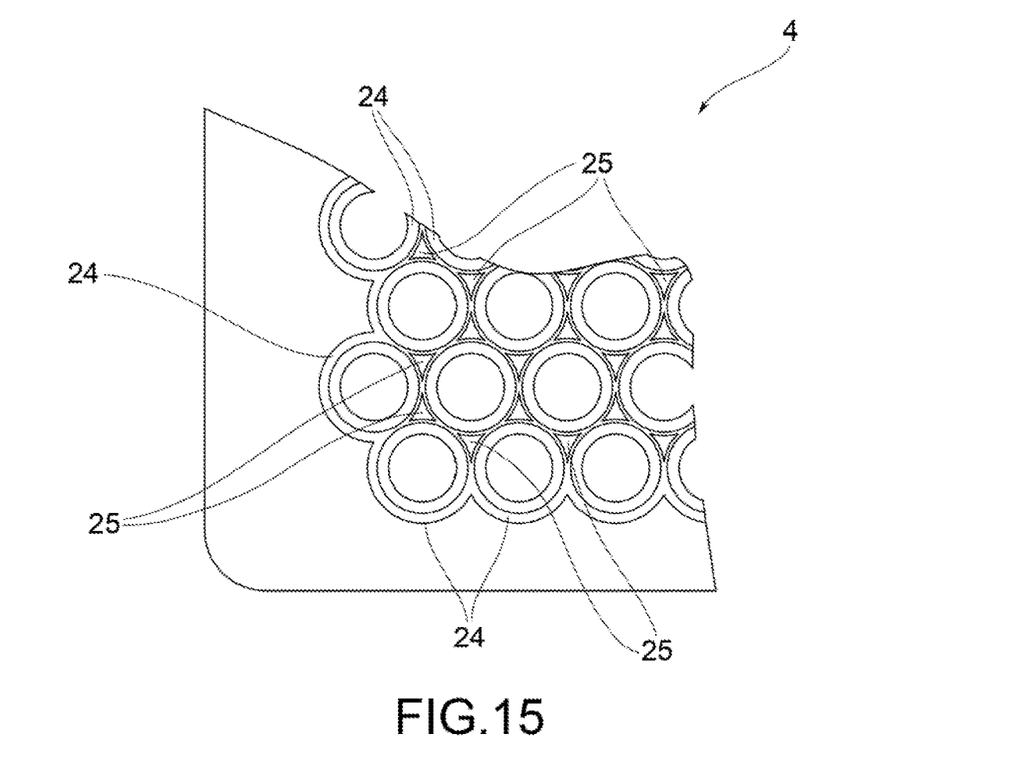

The perimeter walls 24 of adjacent seats may be tangent to each other, i.e. in direct contact, defining a plurality of through holes 25, such as, for example, illustrated in FIG. 15.

According to an embodiment, the perimeter walls 24 of seats 16 neighboring or adjacent to each other are separated by a lattice structure 36 comprising a plurality of spacers 40.

Figure 14:
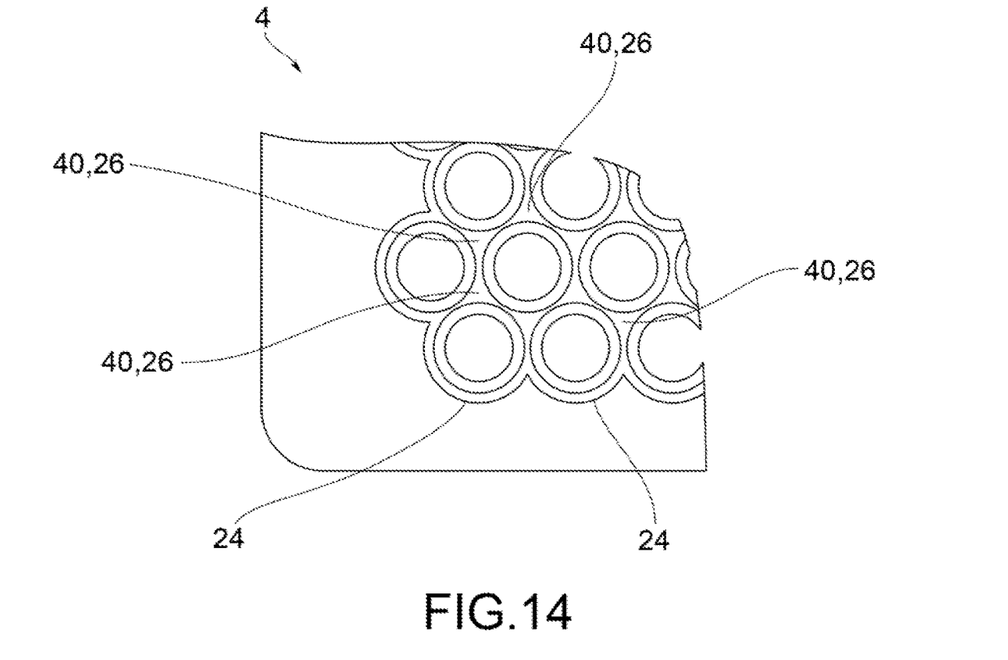
FIGS. 14 and 15 show a plan view from above of a detail of the structure for packaging containers for pharmaceutical use of FIG. 13, according to two possible variant embodiments of the present invention.

The spacers may be made up of closed walls 26 (as for example illustrated in FIG. 14).

The perimeter walls 24 of the seats 16 are preferably cylindrical relative to a cross-section plane perpendicular to said main extension axes X-X.

Preferably, the perimeter walls 24 have a circular cross-section relative to a cross-section plane perpendicular to said main extension axes X-X.

Obviously, the geometry of the seats 16 is functional to the containment of the respective containers for pharmaceutical use 20, whereby it is possible to modify the geometry of the seats 16 according to the geometry of said containers for pharmaceutical use 20. For example, alternatively, the geometry of the seats 16 could also have a frusto-conical or star shape.

Moreover, said seats 16 must be dimensioned in such a way that they may accommodate containers for pharmaceutical use 20 with slight play, which may facilitate both their insertion and subsequent extraction.

On the side of a top face 44 of the seats 16, intended to receive in abutment an undercut element 48 of said containers 20, a raised perimeter 52 is provided suitable to delimit and surround at least partially an annular pocket 56, enlarged with respect to the seat 16 and intended to house and to receive in abutment the undercut element 48 of said containers 20.

The raised perimeter 52 may be continuous or even discontinuous, for example comprising a plurality of pegs interspersed with empty spaces.

Preferably, the annular pocket 56 has a support plane 60, intended to receive in abutment the undercut element 48 of said containers 20, perpendicular to the main extension axes X-X.

Such perpendicularity guarantees the correct positioning of containers for pharmaceutical use 20 within the seats 16, so that they are all parallel to the main extension axes X-X.

The undercut element 48 undercuts a main body 50 of the container 20, which is inserted into the seat 16 and locked in place along the main extension axis X-X following contact between the undercut element 48 and the support plane 60 of the annular pocket 56.

It should be noted that the undercut element 48 may be of any shape and may be positioned either at an end of the container for pharmaceutical use 20 or in an intermediate position thereof.

Preferably, the undercut element 48 is counter-shaped to the corresponding annular pocket 16.

Figure 1:
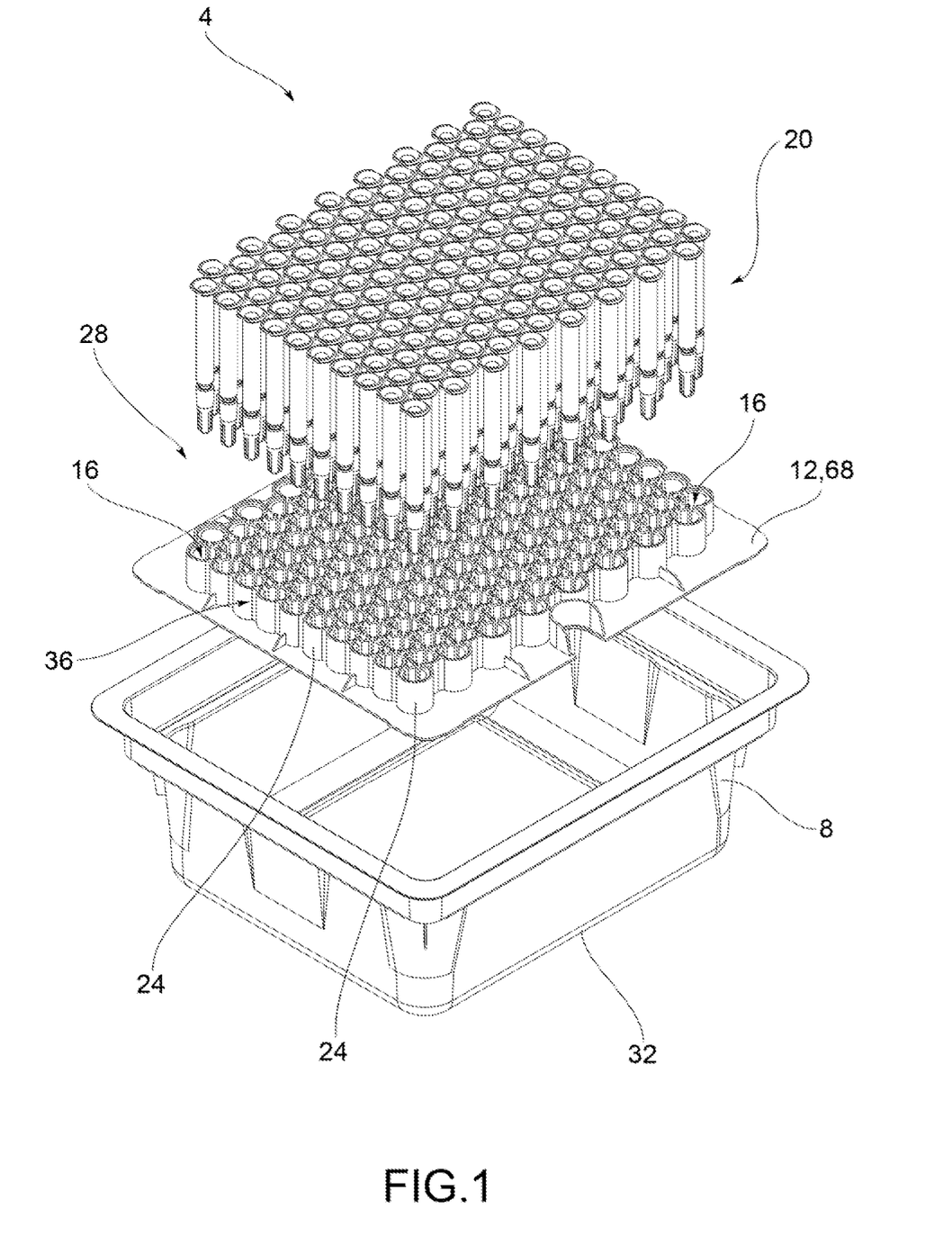
FIG. 1 shows an exploded perspective view of a structure for packaging containers for pharmaceutical use according to the present invention.
Figure 2:
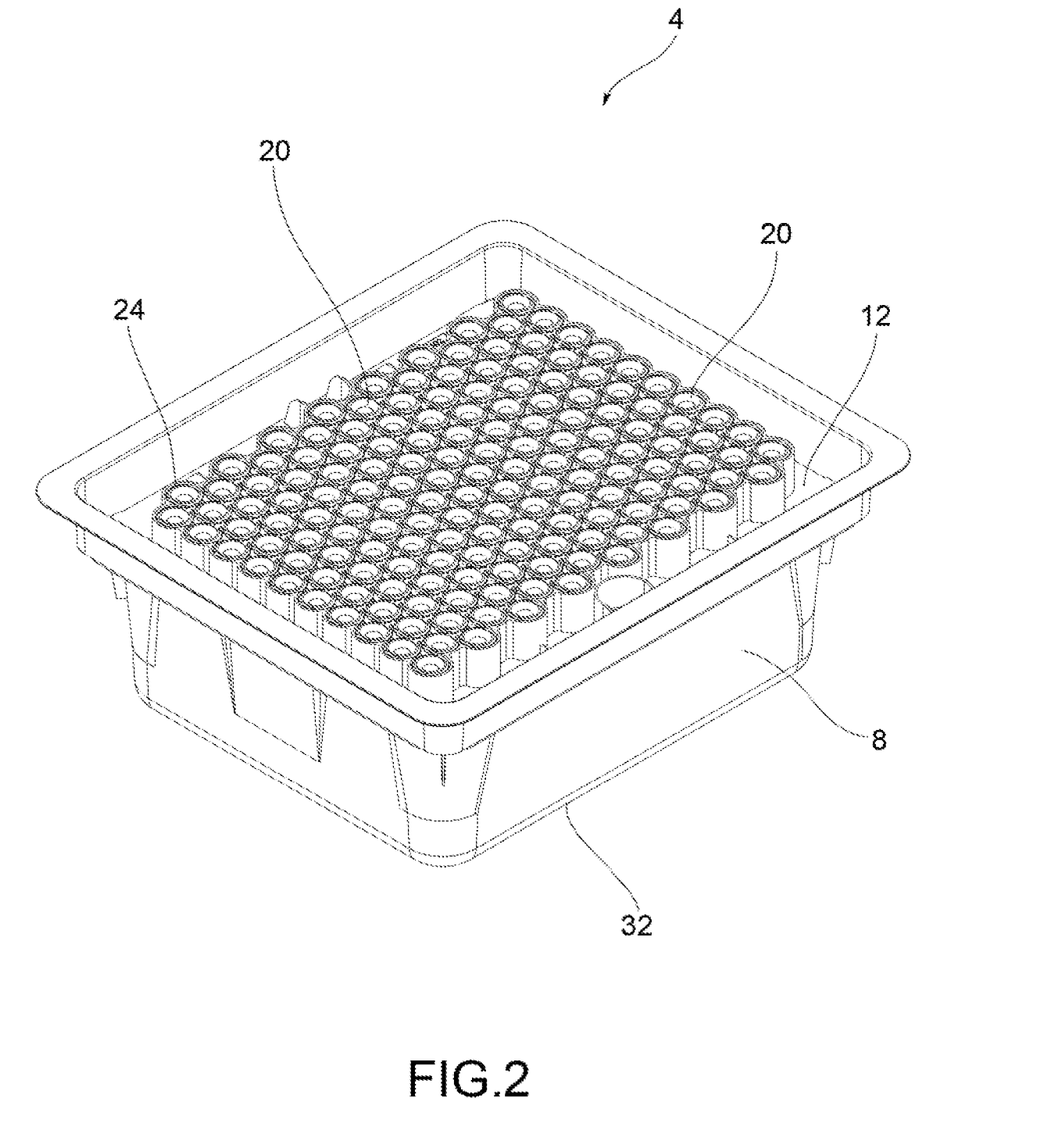
FIG. 2 shows a perspective view, in assembled configuration, of the containment structure of FIG. 1.
Figure 3:
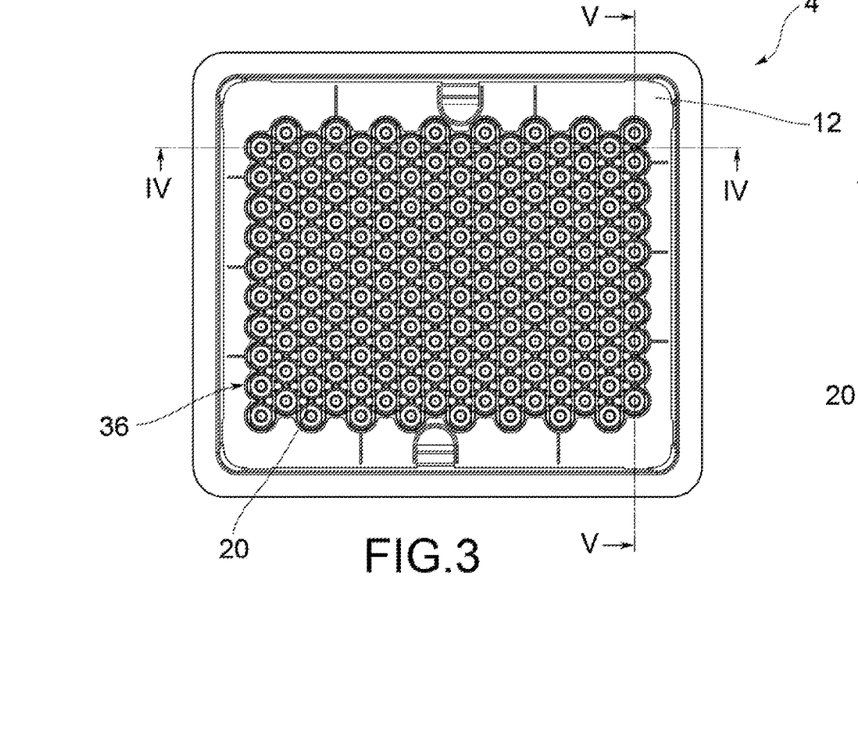
FIG. 3 shows a plan view of the containment structure in FIG. 1.
Figure 4:
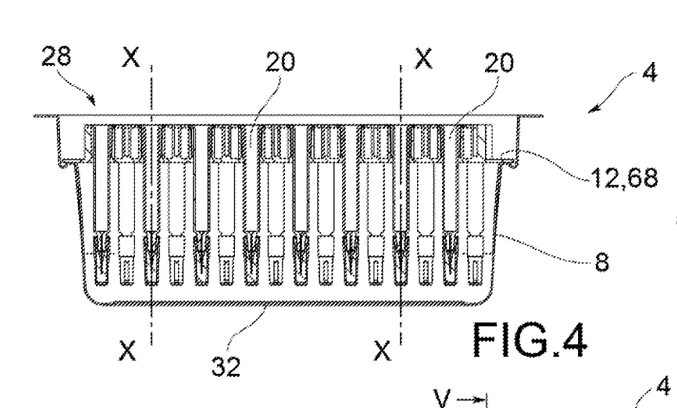
FIG. 4 shows a view in cross-section of the containment structure of FIG. 2 along the cross-section plane IV-IV indicated in FIG. 3.
Figure 5:
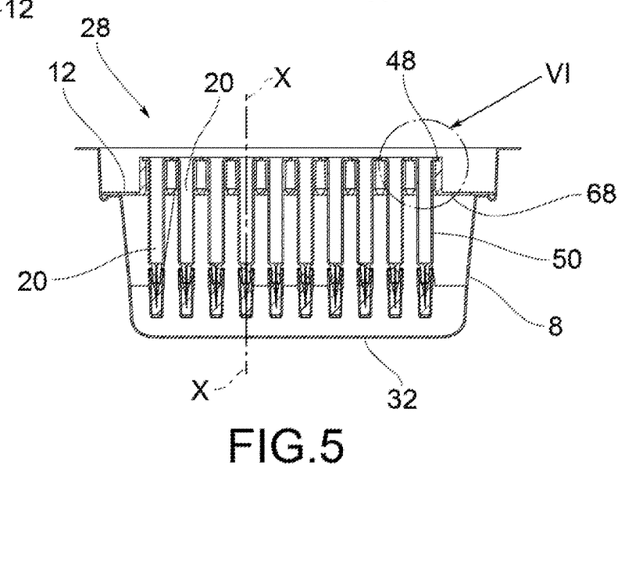
FIG. 5 shows a view in cross-section of the containment structure of FIG. 1 along the cross-section plane V-V indicated in FIG. 3.
Figure 6:
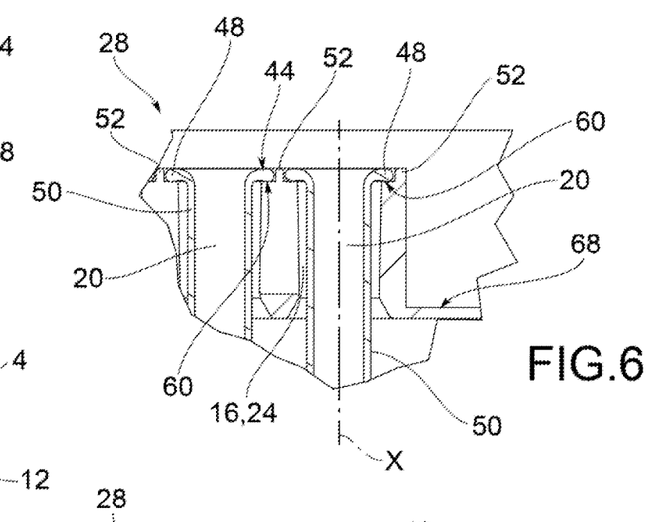
FIG. 6 shows the enlarged detail VI of FIG. 5.
Figure 7:
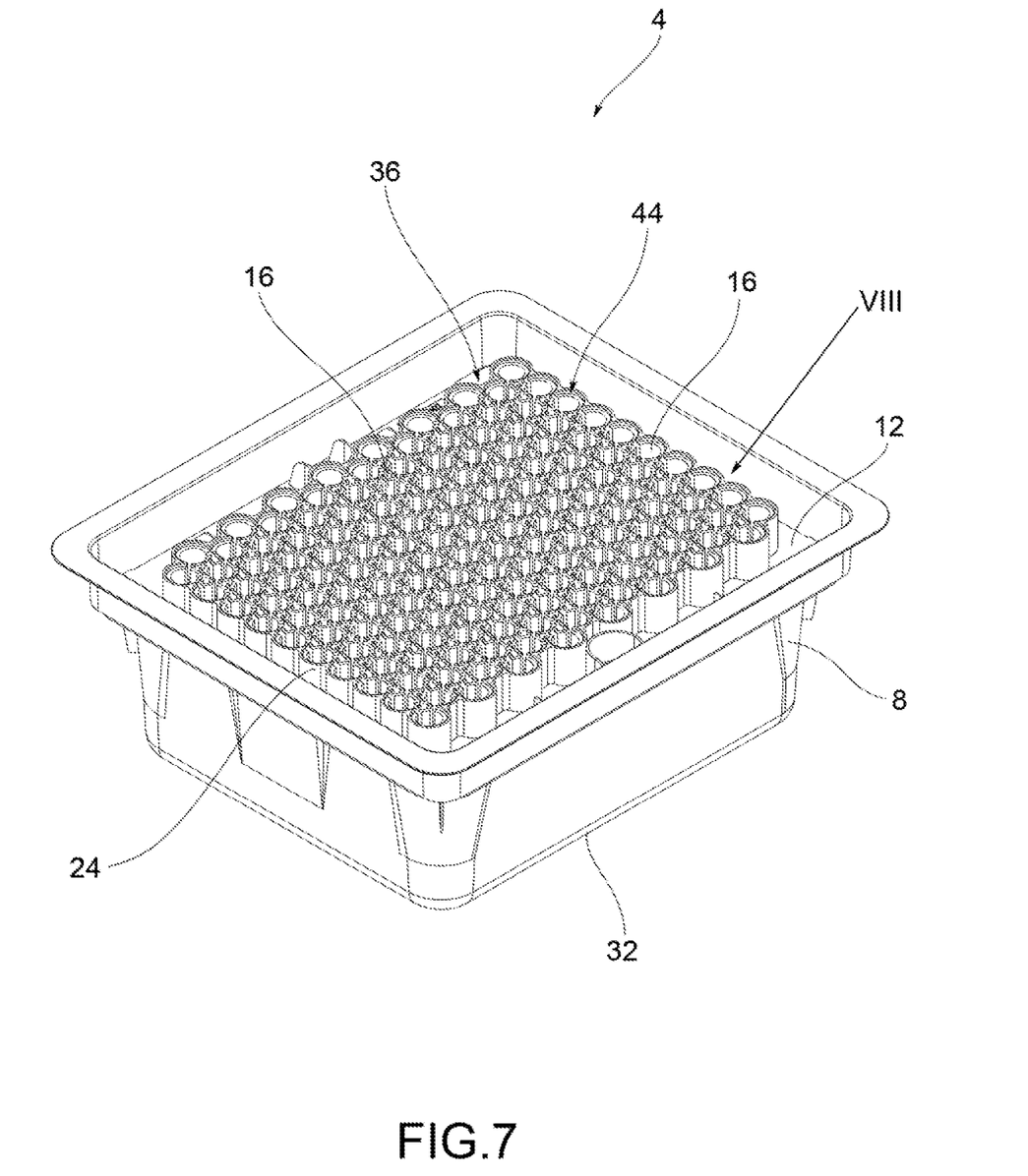
FIG. 7 shows a perspective view, in an assembled configuration, of the structure for packaging containers for pharmaceutical use in FIG. 2, without containers for pharmaceutical use.
Figure 8:
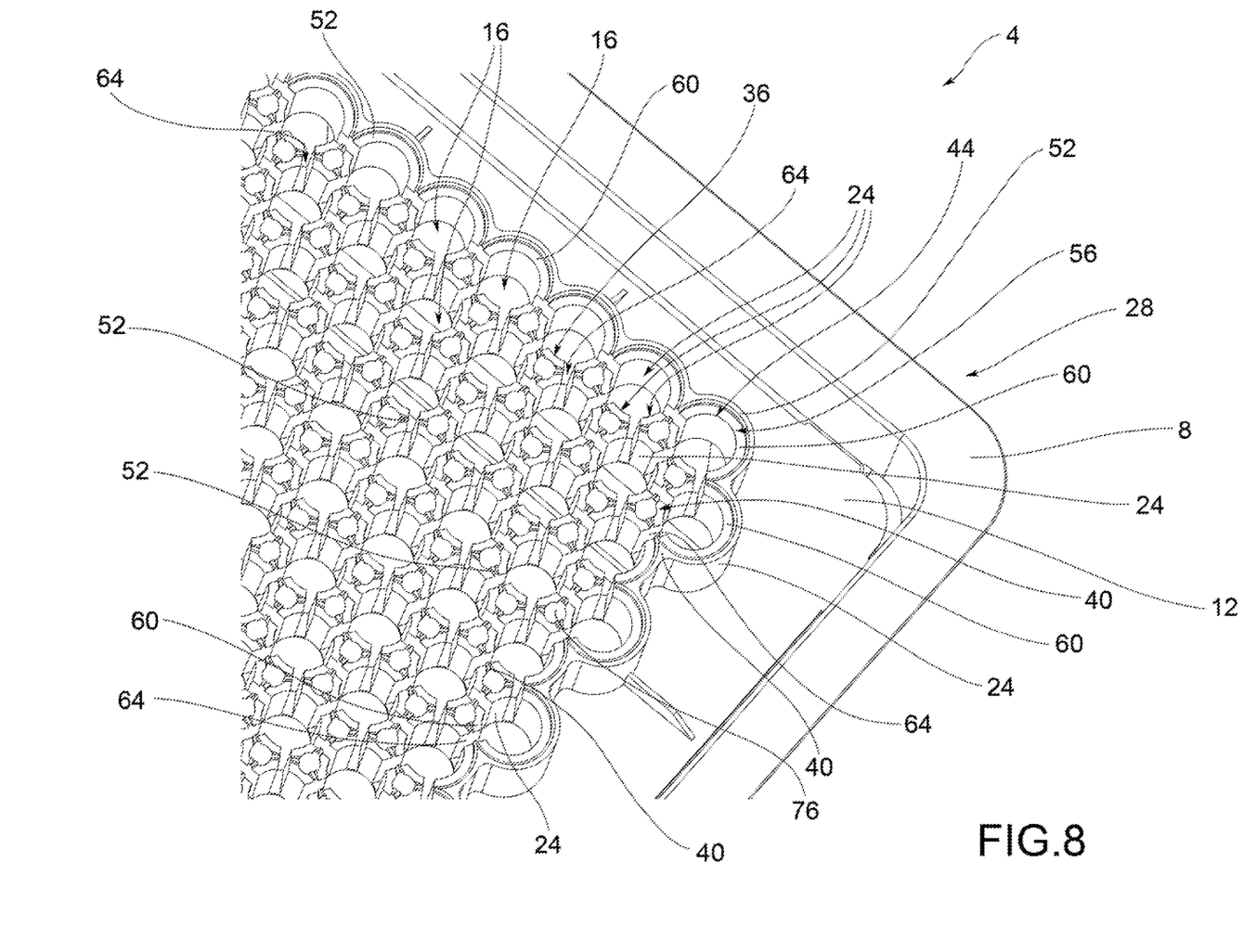
FIG. 8 shows the enlarged detail VIII of FIG. 7.
Figure 9:
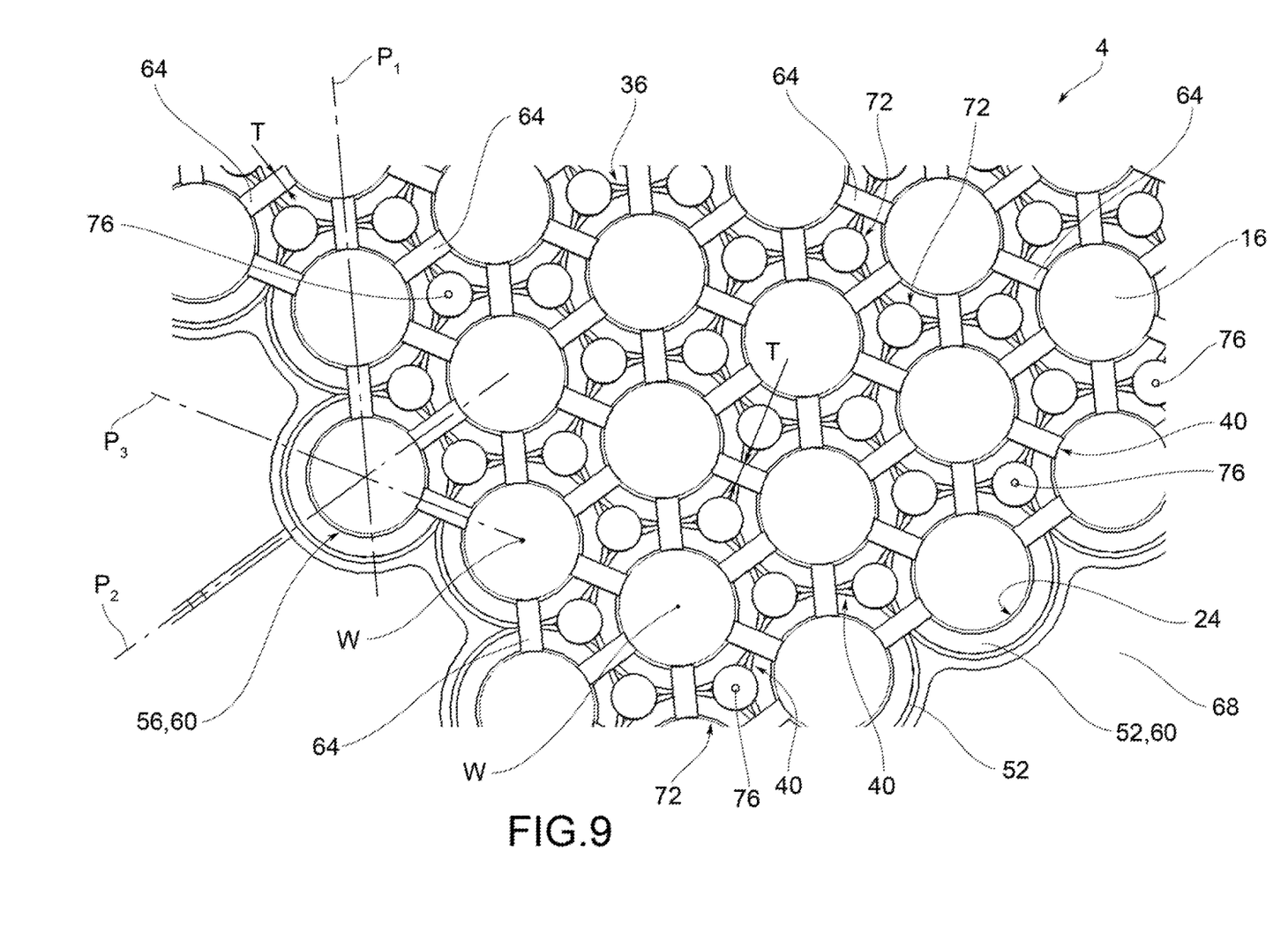
FIG. 9 shows a plan view from the top of a portion of the structure in FIG. 7.
Figure 10:
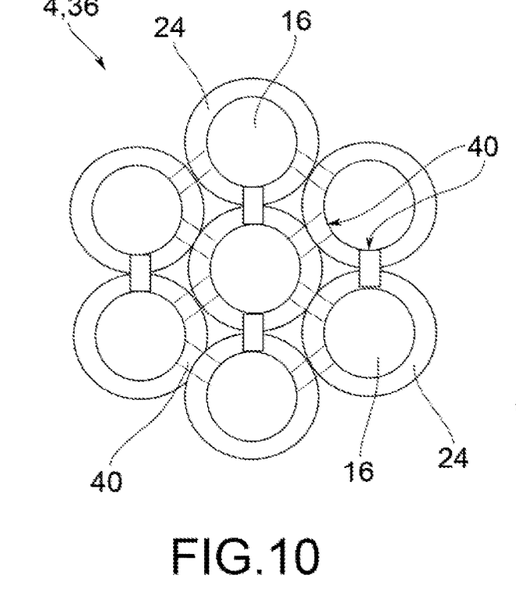
FIGS. 10-11 show a plan view, respectively with and without containers for pharmaceutical use, of a containment structure according to a further embodiment of the present invention.
Figure 11:
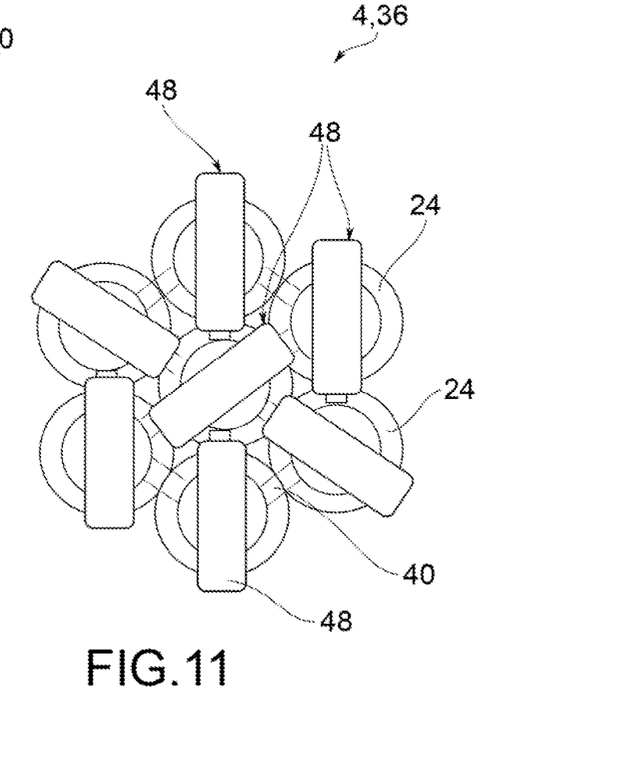

According to an embodiment, the undercut element 48 and the annular pocket 16 have an asymmetric geometry relative to the corresponding main extension axis X-X, so as to orient the container for pharmaceutical use 20 with respect to a rotation about said main extension axis X-X, following the insertion of the undercut element 48 into the relative annular pocket 56 (FIG. 11).

This asymmetric or non-axial-symmetric geometry relative to the main extension axis X-X, allows the orientation of the undercut elements 48 such as flanges or collars; in the case of flanges or non-circular collars, this support plane 12 maximizes the density of containers for pharmaceutical use 20 by available surface area (FIG. 11).

In a preferred embodiment, the spacers 40 comprise at least one notch or interruption 64 extending from the side of the upper face 44 to a lower face 68 of the support plane 12, opposite the upper face 44.

The notch or interruption 64 is blind or does not pass through the side of the bottom face 68.

Therefore, the notch or interruption 64 does not interrupt the continuity of the support plane 12.

Preferably, said notches or interruptions 64 extend, parallel to the main extension axes X-X, for at least 10% of the distance between the upper face 44 of the seats 16 and the lower face 68 of the support plane 12.

According to an embodiment, the notch or interruption 64 is oriented along a radial direction relative to each seat 16, passing through an axis of axial symmetry W of each seat 16.

The notches or interruptions 64 of two neighboring seats 16 create communicating openings between said neighboring seats 16: in other words, the notches or interruptions 64 concern the entire thickness of the spacers 40 relative to a plane perpendicular to the main extension axes X-X so as to lead into the neighboring seats 16 thereof.

According to a possible embodiment, the notches or interruptions 64 of two neighboring seats 16 connect the axes of symmetry W of said neighboring seats 16.

Preferably, all the notches or interruptions 64 are parallel to three main directions P1, P2, P3 which form in pairs an acute angle of 60°.

In particular, directions parallel to said three directions P1,P2,P3 intersect the axes of symmetry W of all the seats 16 of the lattice structure 36.

This geometric arrangement allows simultaneously for a good lightness of the structure to be obtained, due to the presence of notches or interruptions 64, but also a high mechanical stiffness, due to the orientation of the notches or interruptions 64 with respect to the positions of the seats 16.

According to a possible embodiment, the perimeter walls 24 of the neighboring seats 16 are tangent to each other at said notches or interruptions 64: in this way a high density is obtained, and thus good packing density, for the seats 16, relative to the overall extension of the containment structure 4. The preceding condition allows for a large number of containers 20 to be contained.

Preferably, the seats 16 within the lattice structure 36 are arranged in a quincunx pattern. In addition, preferably, the axes of symmetry W of three neighboring seats 16, arranged to form a triangle, are equidistant from each other to form an equilateral triangle.

According to this embodiment, wherein the perimeter walls 24 of each seat 16 alternate with the notches 64 so as to form a circular geometry of the seat 16, the lattice structure 36 defines an island 72 of separation between three neighboring seats 16, said island 72 being delimited by the perimeter walls 24 of said neighboring seats 16 and by three notches or interruptions 64, so that each notch or interruption 64 separates said neighboring seats 16 into distinct pairs.

Said islands 72 support at least partially the raised perimeters 52.

For example, each island 72 has a substantially hexagonal cross-sectional shape, wherein three sides are straight and define edges of said notches or interruptions 64 and the other three sides are curved and define portions of the seats 16 for housing containers for pharmaceutical use 20.

Depending on a possible embodiment, each island 72 has a central hole or lightening hole 76 extending from the raised perimeter 52 of the upper side 28 to the lower face 68, opposite the upper side 28.

Said central hole or lightening hole 76 further contributes to reducing the collective mass of the containment structure 4.

According to a possible embodiment, the central hole or lightening hole 76 is blind or does not pass through the side of the lower face 68.

According to a further possible embodiment, the hole or lightening hole 76 passes through the lower face 68.

According to a further possible embodiment, the islands 72 do not have the hole or lightening hole 76.

As seen, to preserve the condition of high cleanliness by limiting the risk of particle contamination of containers for pharmaceutical use 20, it is possible, during filling, to use an air flow to create a sort of barrier to the intrusion of external agents and any impurities.

For this purpose, it is therefore essential that the support plane 12 is as pervious as possible to this flow not so much at the seats 16, which, when occupied by the containers for pharmaceutical use 20, do not allow the passage of air, but specifically in the area between the neighboring seats that always opposes the passage of air, creating negative turbulence.

Making central through holes or lightening holes 76 allows an easy penetration of the containment structure 4 by the air flow which meets a reduced resistance and therefore may act in conditions of substantially laminar flow, improving the condition of a low level of particle contamination in the stages of treatment and filling of containers for pharmaceutical use 20.

Therefore, the symmetry and/or repetition of the interstitial geometry with central through holes or lightening holes 76, arranged between the various seats 16 facilitates the passage of a laminar air flow that surrounds the seats 16 and protects them from the entry of external agents or impurities.

The structure for the packaging of containers for pharmaceutical use comprises, as seen, at least one container for pharmaceutical use 20 with an undercut element 48 and a main body 50.

The main body 50 is housed inside the seat 16 and the undercut element 48 is housed with play inside the annular pocket 56, in abutment against the upper face 44 of the seat 16. Said lateral or radial play is less than or equal to a width T of the notch or interruption 64, said width T being the minimum distance between mutually facing free walls that delimit the notch or interruption 64.

In this way, the very presence of the container 20 prevents the complete closure of the interruption or notch 64 due to the weight of the containment structure 4 and the container itself. In effect, in the case of downward elastic flexing, which would tend to close the interruption or notch 64, the interference between the undercut element 48 and the annular pocket 56 creates an end stop to the flexing or elastic deformation of the structure.

In other words, once the container has been inserted into its seat, it becomes a structural stiffening element, once the play between the undercut element 48 and the raised perimeter of the annular pocket 56 has been eliminated.

As may be appreciated from the foregoing, the present invention allows the drawbacks of the prior art to be overcome.

In effect, the structure has a mechanical stiffness and/or a geometric shape sufficient to guarantee a reduced elastic flexing of the structure under its own weight and that of the containers supported thereby, with particular reference to the condition wherein the latter are filled.

This ensures that the containers are always correctly aligned within their respective seats, even under conditions of maximum load of the structure and its containers, for example in the case of containers filled with medicine.

Moreover, any risk of contact between the collars of neighboring containers is prevented, since the collars are contained within pockets or seats delimited by the raised perimeters.

Therefore, said raised perimeters, for example in the form of pins or protuberances, prevent any type of contact between the collars of neighboring containers.

Moreover, due to the notches on the perimeter walls and the holes in the islands, a significant reduction in weight is obtained; such reduction in weight does not affect the mechanical resistance since, once the containers are positioned, the relative collars prevent said notches from closing up as a result of the weight of the same containers.

Therefore, the containers, while increasing the collective weight of the containment structure, become structural stiffening elements of the support plane (nest) and their very presence stiffens the overall structure. In effect, the radial play between the collars and the circumferential elevations (protuberances or pins) is very limited, whereby in case of downward elastic flexing of the support plane due to the weight, the notches (which open upwards) would tend to close radially, tightening against the same collars. Such small amount of radial play in effect prevents the closure of the notches and therefore stiffens the structure as a whole because obviously the presence of the collars prevents the closure of the notches.

In the absence of the containers, the stiffening effect provided by the collars is obviously missing, but the structure is considerably lighter precisely because of the absence of the additional weight due to the same containers.

The parallelism between the containers relative to a vertical direction is guaranteed not only by the high structural rigidity of the containment structure but also by the fact that the collars rest in abutment against a planar edge with a circular crown shape, since said edge is in turn perpendicular to said vertical direction.

Moreover, the presence of the raised perimeters also guarantees the correct radial distance between the containers and thus allows the grippers of a manipulator to be inserted without impact in the gaps between adjacent containers. Such correct radial distance further helps to avoid the risk of accidental impacts between neighboring containers.

In addition, the structure according to the present invention allows an adequate perviousness to the passage of a laminar flow to be obtained.

In particular, at the time of use, the primary containers are normally introduced into a particle contamination control area, e.g. ISO5-controlled atmosphere or sterile clean rooms, to undergo an aseptic filling process. Such filling step provides for unpacking the packaging structures sealed inside their protective wrappings, opening the protective wrappings through a contamination control process (typically through the effect of a laminar flow of ultra-clean air so as to create a barrier to external contaminants), extracting the packaging structures from their protective wrapping after biological decontamination of the outer surface, then proceeding with positioning each packaging structure within the aseptic zone before removing the permeable membrane of the tray.

At this stage, due to the presence of through holes, it is possible to create a substantially laminar air flow that allows effective barriers against external contaminants to be obtained.

A person skilled in the art, in the object of satisfying contingent and specific requirements, may make numerous modifications and variations to the structures described above, all of which are within the scope of the invention as defined by the following claims.

The invention claimed is:

1. Structure for packaging containers for pharmaceutical use comprising:
a support plane fitted with a plurality of seats for housing containers for pharmaceutical use, the seats having main extension axes, parallel to each other,
the seats being delimited by perimeter walls which project from the support plane towards a top side of the structure,
wherein
on the side of a top face of the seats, intended to receive in abutment an undercut element of said containers, a raised perimeter of each seat is provided to delimit and surround at least partially an annular pocket, enlarged with respect to the seat and intended to receive in abutment the undercut element of said containers for pharmaceutical use.

2. Structure for packaging containers for pharmaceutical use according to claim 1, wherein the annular pocket has a support surface, intended to receive in abutment the undercut element of said containers, perpendicular to the main extension axes.

3. Structure for the packaging of containers for pharmaceutical use according to claim 1 wherein the perimeter walls of the seats are cylindrical with a circular cross-section with respect to a cross-section plane perpendicular to said main extension axes.

4. Structure for the packaging of containers for pharmaceutical use according to claim 1, wherein the perimeter walls of adjacent seats are tangent to each other, defining a plurality of through holes.

5. Structure for the packaging of containers for pharmaceutical use according to claim 1, wherein the perimeter walls of neighboring seats are spaced from each other by means of a lattice structure comprising a plurality of spacers.

6. Structure for the packaging of containers for pharmaceutical use according to claim 5, wherein said spacers comprise closed walls.

7. Structure for the packaging of containers for pharmaceutical use according to claim 5, wherein said spacers comprise at least one notch or interruption extending from the side of the top face towards a bottom face of the support plane, opposite the top face, the notch or interruption being blind or not through on the side of the bottom face.

8. Structure for the packaging of containers for pharmaceutical use according to claim 7, wherein said notches or interruptions extend, parallel to the main extension axes, for at least 10% of the distance between the top face of the seats and the bottom face of the support plane.

9. Structure for the packaging of containers for pharmaceutical use according to claim 7, wherein said notch or interruption is oriented along a radial direction relative to each seat, passing through an axis of axial symmetry of each seat.

10. Structure for the packaging of containers for pharmaceutical use according to claim 7, wherein the notches or interruptions of two neighboring seats place said neighboring seats in communication with each other.

11. Structure for the packaging of containers for pharmaceutical use according to claim 7, wherein the notches or interruptions of two neighboring seats connect the axes of symmetry of said neighboring seats with each other.

12. Structure for the packaging of containers for pharmaceutical use according claim 7, wherein all the notches or interruptions are parallel to three main directions which form in pairs an acute angle of 60°.

13. Structure for the packaging of containers for pharmaceutical use according to claim 12, wherein directions parallel to said three main directions intersect axes of symmetry of all the seats of the lattice structure.

14. Structure for the packaging of containers for pharmaceutical use according to claim 7, wherein the perimeter walls of neighboring seats are tangent to each other at said notches or interruptions.

15. Structure for the packaging of containers for pharmaceutical use according to claim 7, wherein the lattice structure identifies an island of separation between three neighboring seats said island being delimited by the perimeter walls of said neighboring seats and by three notches or interruptions, each notch or interruption connecting the open spaces of different pairs of said neighboring seats with each other.

16. Structure for the packaging of containers for pharmaceutical use according to claim 15, wherein each island has a hexagonal cross-section shape, wherein three sides are straight and define edges of said notches or interruptions and three sides are curved and define portions of the seats for housing containers for pharmaceutical use.

17. Structure for the packaging of containers for pharmaceutical use according to claim 15, wherein each island has a central hole or lightening hole extending from the top side to a bottom side, opposite the top side.

18. Structure for the packaging of containers for pharmaceutical use according to claim 17, wherein the hole or lightening hole passes through the bottom side.

19. Structure for the packaging of containers for pharmaceutical use according to claim 17, wherein the hole or lightening hole is blind or does not pass through the side of the bottom face.

20. Structure for the packaging of containers for pharmaceutical use according to any one of the claim 15, wherein said islands support at least partially the raised perimeters.

21. Structure for the packaging of containers for pharmaceutical use according to claim 1, wherein the seats inside the lattice structure are arranged in a quincunx.

22. Structure for the packaging of containers for pharmaceutical use according to claim 1, wherein axes of symmetry of three neighboring seats, arranged to form a triangle, are equidistant from each other to form an equilateral triangle.

23. Structure for the packaging of containers for pharmaceutical use according to claim 1, comprising at least one container for pharmaceutical use having an undercut element and a main body, the main body being housed inside the seat, the undercut element abutting at least partially against a support plane of the annular pocket.

24. Structure for the packaging of containers for pharmaceutical use according to claim 23, wherein the undercut element is counter-shaped to the corresponding annular pocket.

25. Structure for the packaging of containers for pharmaceutical use according to claim 23, wherein the undercut element and annular pocket have an asymmetric geometry relative to the corresponding main extension axis, so as to orient the container for pharmaceutical use, relative to a rotation around said main extension axis, following the insertion of the undercut element in the relative annular pocket.

26. Structure for the packaging of containers for pharmaceutical use according to claim 23, in combination with claim 5, wherein the undercut element is housed with play inside an annular pocket, in abutment against a support plane of the annular pocket, wherein said play is less than or equal to a width of the notch or interruption, said width being the minimum distance between the reciprocally facing free walls delimiting the notch or interruption.

* * * * *